(12) United States Patent
Wienand et al.

(10) Patent No.: US 10,060,876 B2
(45) Date of Patent: Aug. 28, 2018

(54) GAS SENSOR FOR MEASURING DIFFERENT GASES, AND CORRESPONDING PRODUCTION METHOD

(71) Applicants: Heraeus Sensor Technology GmbH, Hanau (DE); Ilse Ullrich, Großheubach (DE)

(72) Inventors: Karlheinz Wienand, Aschaffenburg (DE); Karl-Heinz Ullrich, Großheubach (DE); Matsvei Zinkevich, Goldbach (DE)

(73) Assignee: Heraeus Sensor Technology GmbH, Hanau (DE)

( * ) Notice: Subject to any disclaimer, the term of this patent is extended or adjusted under 35 U.S.C. 154(b) by 73 days.

(21) Appl. No.: 14/897,148

(22) PCT Filed: May 28, 2014

(86) PCT No.: PCT/EP2014/061065
§ 371 (c)(1),
(2) Date: Dec. 9, 2015

(87) PCT Pub. No.: WO2014/198540
PCT Pub. Date: Dec. 18, 2014

(65) Prior Publication Data
US 2016/0109403 A1    Apr. 21, 2016

(30) Foreign Application Priority Data

Jun. 11, 2013  (DE) .................. 10 2013 210 903

(51) Int. Cl.
*G01N 27/407*     (2006.01)
*G01M 15/10*      (2006.01)

(52) U.S. Cl.
CPC ...... *G01N 27/4075* (2013.01); *G01M 15/102* (2013.01); *G01N 27/407* (2013.01)

(58) Field of Classification Search
CPC ...... G01N 27/28; G01N 27/30; G01N 27/403; G01N 27/406; G01N 27/4067;
(Continued)

(56) References Cited

U.S. PATENT DOCUMENTS 4,409,183 A * 10/1983 Fischer .............. G01N 27/4161
                                                    204/400
4,505,805 A *  3/1985 Mase ................. G01N 27/4065
                                                    204/412

(Continued)

FOREIGN PATENT DOCUMENTS

DE     19757112 A1    4/1999
DE     19651328 B4    7/2007
(Continued)

OTHER PUBLICATIONS

International Search Report (with English translation) and Written Opinion dated Aug. 7, 2014 in International Application No. PCT/EP2014/061065.

(Continued)

*Primary Examiner* — Benjamin Schmitt
(74) *Attorney, Agent, or Firm* — Panitch Schwarze Belisario & Nadel LLP

(57) ABSTRACT

A gas sensor for measuring the concentrations of gases includes a solid body electrolyte, at least three electrodes, and a closed chamber. The doped platinum includes at least 50% by weight platinum and the remainder includes at least one further element selected from the group of solid body electrolytes. In particular, the doped platinum includes between 0.5% by weight to 15% by weight $ZrO_2$ and the remainder is platinum, or the pure platinum is 100% by weight platinum and the gold alloy comprises at least 50% by weight gold and maximally 50% by weight platinum. In particular, the gold alloy includes approximately 85% by weight gold and approximately 15% by weight platinum or (Continued)

the gold alloy comprises at least gold and platinum at a ratio of 85% gold to 15% platinum.

13 Claims, 4 Drawing Sheets

(58) Field of Classification Search
CPC ............ G01N 27/407; G01N 27/4073; G01N 27/4075; G01N 27/4076; G01N 33/0004; G01N 33/0009; G01N 33/0027; G01M 15/10; G01M 15/102; G01M 15/104
USPC .................. 73/23.2, 23.31, 31.05, 31.06
See application file for complete search history.

(56) References Cited

U.S. PATENT DOCUMENTS

| | | | | |
|---|---|---|---|---|
| 5,989,624 | A * | 11/1999 | Kida | G01N 27/4075 |
| | | | | 204/421 |
| 6,303,011 | B1 * | 10/2001 | Gao | G01N 27/4074 |
| | | | | 204/425 |
| 2002/0108856 | A1 | 8/2002 | Kunimoto et al. | |
| 2002/0117397 | A1 * | 8/2002 | Anderson | G01N 27/4075 |
| | | | | 204/424 |
| 2003/0121801 | A1 * | 7/2003 | Inaba | G01N 27/4075 |
| | | | | 205/785.5 |
| 2005/0016841 | A1 * | 1/2005 | Chang | G01N 27/4071 |
| | | | | 204/280 |

FOREIGN PATENT DOCUMENTS

| | | |
|---|---|---|
| DE | 1020070448049 A1 | 4/2009 |
| DE | 102008054617 A1 | 6/2010 |
| DE | 102009054889 A1 | 6/2011 |
| DE | 102010040194 A1 | 3/2012 |
| EP | 2226628 A1 | 9/2010 |
| JP | H08510840 A | 11/1996 |
| JP | H10239276 A | 9/1998 |
| JP | 2004177322 A | 6/2004 |
| WO | 2009046927 A2 | 4/2009 |
| WO | 2010072460 A1 | 7/2010 |

OTHER PUBLICATIONS

Office Action dated Apr. 29, 2014 in DE Application No. 102013210903.2.
Office Action dated Dec. 20, 2016 in JP Application No. 2016-518906.
Office Action dated Aug. 7, 2017 in JP Application No. 2016-518906.
English Translation of Search Report Accompanying Office Action dated Jan. 19, 2018 in CN Application No. 20140033112.5.

* cited by examiner

GAS SENSOR FOR MEASURING DIFFERENT GASES, AND CORRESPONDING PRODUCTION METHOD

CROSS-REFERENCE TO RELATED APPLICATIONS

This application is a Section 371 of International Application No. PCT/EP2014/061065, filed May 28, 2014, which was published in the German language on Dec. 18, 2014, under International Publication No. WO 2014/198540 A1, and the disclosure of which is incorporated herein by reference.

BACKGROUND OF THE INVENTION

The present invention relates to a gas sensor for measuring the concentrations of gases, in particular of oxygen and at least one further gas, preferably of at least one oxidizable exhaust gas component in the form of a further gas. Moreover, the present invention relates to a device for producing gas sensors, a method for producing gas sensors, a method for measuring the concentrations of gases, a gas sensor device, and the use of a gas sensor.

It is known from DE 196 51 328 B4 that oxygen pumps are based on an electrochemical reaction of zirconium dioxide ($ZrO_2$) between two electrodes. In the oxygen pump, oxygen is transported and/or pumped from one side of a zirconium dioxide wall to the other side by means of the oxygen being reduced to oxygen ions on the cathode, subsequent ion migration of the oxygen ions in the zirconium dioxide, and, lastly, oxidation of the oxygen ions to oxygen on the anode. Due to this effect, a difference in partial pressure on the two sides of the oxygen pump can be attained.

A gas sensor allowing exhaust gas components to be measured is known from DE 10 2007 048 049 A1. The gas sensor comprises a substrate having an electrically insulating surface, for example a body made of $Al_2O_3$. In DE 10 2007 048 049 A1, the body is coated with a heating resistor on which a lid made of an ionic conductor (according to DE 10 2007 048 049 A1 this would be an ion conductor made of zirconium dioxide), and the substrate surface forms a hollow space. Metallically conductive electrodes are arranged above and below the ion conductor and two of these are provided as platinum electrodes. Moreover, the gas sensor on the ion conductor comprises a further electrode that is provided as a mixed potential electrode and comprises a precious metal alloy consisting of gold and platinum. The electrodes in this context are porous, such that they are permeable for oxygen. Preferably, they are applied by means of screen printing DE 197 57 112 A1 discloses a gas sensor for measuring oxygen and/or the air/fuel ratio lambda and at least one further gaseous component, such as, for example, hydrocarbons or nitrogen oxides, in gas mixtures by means of a reference electrode representing a' constant oxygen partial pressure, an oxygen ion-conducting solid electrolyte, and at least two measuring electrodes, whereby the measuring electrodes and the reference electrode are arranged directly on the solid electrolyte, and have electrical leads for connecting and for detecting the electrical measuring signals. According to DE 197 57 112 A1, the solid electrolyte is provided to be of any geometrical shape and has a side facing the measured gas and a reference side that is separated from the measured gas, whereby the arrangement of the electrodes with the reference electrode on the reference gas side and the at least two measuring electrodes on the measured gas side concurrently yields at least two measuring signals that are based on identical or different, measuring principles and are based on different gaseous components. The sensor is used, for example, for the motor control of motor vehicles.

It is a disadvantage of the prior art, as currently known, that a precise and rapid measurement for the detection of gas concentrations, for example of gas concentrations in exhaust gases, is difficult, time-consuming, and very elaborate.

BRIEF SUMMARY OF THE INVENTION

It is therefore an objective of the present invention to provide an option for precise, easy, and rapid measurement of the concentrations of different gases and/or changing gas compositions.

In one embodiment, a gas sensor according to the present invention comprises at least one solid body electrolyte, in particular a solid body electrolyte made of at least $ZrO_2$, preferably made of at least 90% by weight $ZrO_2$ and the remainder made of at least one further element from the group consisting of yttrium oxide and/or hafnium oxide. The gas sensor further comprises at least three electrodes, preferably comprising two electrodes made of at least doped platinum or of at least pure platinum and one electrode made of a gold alloy, whereby two electrodes, preferably the one electrode made of the doped platinum or made of the pure platinum and the one electrode made of the gold alloy, are arranged on a top side of the solid body electrolyte and one electrode, preferably the other electrode made of the doped platinum or made of the pure platinum, is arranged on a bottom side of the solid body electrolyte that is situated opposite from the top side. The gas sensor further comprises at least one closed chamber, whereby the bottom side of the solid body electrolyte forms a part of the chamber.

The above-mentioned objective is met in that the doped platinum comprises at least 50% by weight platinum and the remainder comprises at least one further element from the group of solid body electrolytes, in particular in that the doped platinum comprises between 0.5% by weight to 15% by weight $ZrO_2$ and the remainder is platinum, or in that the pure platinum comprises 100% by weight platinum and that the gold alloy comprises at least 50% by weight gold and maximally 50% by weight platinum. In particular, the gold alloy comprises approximately 85% by weight gold and approximately 15% by weight platinum or the gold alloy comprises gold and platinum at a ratio of 85% gold to 15% platinum. Preferably, the gold alloy comprises at least gold and platinum at a ratio of 85% gold to 15% platinum and, in addition, at least 0.5% by weight to 15% by weight of a solid body electrolyte, in particular $ZrO_2$.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
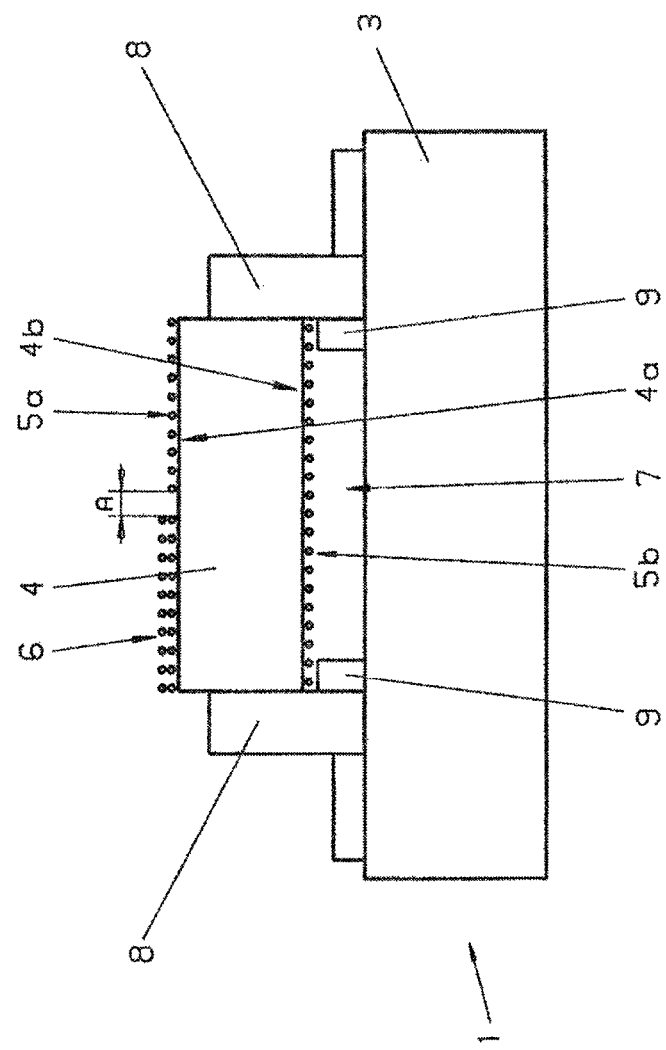
FIG. 1 shows a detail of a gas sensor 1 for measuring concentrations of gases according to an embodiment of the present invention.

It is advantageous that the fractions according to the present invention, namely the fractions of the doped platinum or of the pure platinum and of the gold alloy, render rapid, simple, and precise measurement of the gas concentrations feasible.

It is feasible to measure reducing gases, for example carbon monoxide, for example in an exhaust gas of a heating plant in the exhaust pipe thereof, independent of the season and thus independent of the outside temperature and of the gas composition of the exhaust gas. As a result, for example, different gas compositions of exhaust gas such as those that are present, for example, in Scandinavian gas and Russian gas, can be measured by the gas sensor according to the present invention, and thus also by the gas sensor device according to the present invention.

The electrode made of doped platinum or pure platinum that is preferably arranged below the solid body electrolyte, whereby the solid body electrolyte, acting as oxygen ion conductor, transports oxygen ions through itself as a solid body electrolyte, serves as a reference electrode, whereby the reference electrode, according to the present invention, is arranged in the closed chamber in the gas sensor.

According to the present invention, the closed chamber is such that the electrode that is made of doped platinum or pure platinum and is arranged below the solid body electrolyte has an opposite electrically insulating layer arranged opposite from it and at a distance, for example a small plate or a body made of $ZrO_2$ or $Al_2O_3$. The electrically insulating layer can, in addition, comprise a glass passivation in the chamber area.

The sealing of the chamber, due to the distance on the respective sides or side walls, is accomplished, for example, by a glass seal and/or a platinum paste which are each arranged on the sides or side walls. The chamber particularly preferably comprises both a glass seal and, in addition, a platinum paste on the respective sides or side walls of the chamber. A closed chamber, which is also known by the term of hollow space, is known, for example, from DE 10 2007 048 049 A1.

In a preferred embodiment, the electrode consisting of the gold alloy comprises a layer thickness from 0.1 μm to 50 μm, preferably approximately 5 μm.

In a further advantageous embodiment, the distance between the electrodes on the top side of the solid body electrolyte is between 100 μm and 500 μm, preferably approximately 300 μm.

In a further advantageous embodiment, the electrodes can be applied to the solid body electrolyte by screen printing or dispensing.

In a further advantageous embodiment, the gas sensor allows measurements to be done on oxidizable exhaust gas components, such as hydrogen compounds, nitrogen compounds, in particular nitrogen oxides, ammonia compounds, carbon compounds, in particular carbon monoxides and/or hydrocarbons, or the like.

In accordance with preceding embodiments, a concentration of oxygen can be determined, whereby the concentration is determined by the oxygen pump in the form of the two electrodes made up of pure platinum or doped platinum and the solid body electrolyte. On the other hand, oxidizable compounds can be measured by the mixed potential electrode and the electrode made of pure platinum or doped platinum that is arranged above the solid body electrolyte; i.e. on the surface thereof.

Accordingly, it is feasible to measure a single oxidizable gas compound with a gas sensor according to the present invention or multiple compounds of multiple oxidizable gases in a gas flow with a gas sensor according to the present invention.

The mixed potential electrode for measuring the concentrations of gases other than pure oxygen is formed in the gas sensor from the electrode that comprises the gold alloy.

In a further advantageous embodiment, the gas sensor comprises at least one heating conductor. It is feasible, by the heating conductor, to adjust the operating temperature of the gas sensor appropriately such that a precise, rapid, and simple measurement is made feasible, in particular at low temperatures. This is the case, because the heating conductor heats the gas sensor which enables the transport of oxygen through the solid body electrolyte.

In another advantageous embodiment, at least one gas sensor is arranged on a ceramic substrate, preferably $ZrO_2$ or $Al_2O_3$. The ceramic substrate has an insulating function.

The gas sensor can be called an exhaust gas-sensitive chip, whereby the chip, in this case, preferably comprises the following components: a solid body electrolyte, preferably a solid body electrolyte made of $ZrO_2$ and at least three electrodes, preferably comprising two electrodes made at least of doped platinum or pure platinum and one electrode made of a gold alloy.

In the inventive device for producing gas sensors, the device preferably comprises suitable means for producing a gas sensor and the In the inventive method for producing gas sensors, the gas sensor is preferably produced by a device for producing gas sensors.

In the inventive method for measuring concentrations of gases, in particular of oxygen and at least one further gas, preferably at least one oxidizable exhaust gas component in the form of a further gas, it is preferred to use a gas sensor according to the present invention.

Moreover, the present invention relates to a gas sensor device for measuring the concentrations of gases, in particular of oxygen and at least of one further gas preferably at least of one oxidizable exhaust gas component in the form, of a further gas, whereby the gas sensor device, in an advantageous embodiment, comprises a gas sensor according to the present invention.

The scope of the present invention includes the use of a gas sensor in a combustion engine, in a power plant, preferably in a thermal power plant, in a heating system, preferably in a gas or oil heating system, in a baking oven, in an automobile, preferably in the exhaust gas system of the automobile, in an exhaust gas pipe or in a container, preferably a fruit container.

It is feasible to use a solid body electrolyte made of $CeO_2$ as an alternative to $ZrO_2$ as the solid body electrolyte.

According to the present invention, the solid body electrolytes made up of $ZrO_2$ or $CeO_2$ can be partially or fully stabilized.

The electrode made of doped platinum or pure platinum is also referred to as Pt electrode (platinum electrode). An electrode made of a gold alloy or a doped gold alloy is also referred to as Au electrode (gold-electrode). A doped gold alloy is evident if it comprises, in addition to the gold and platinum fraction of 85% to 15% according to the present invention, at least a supplementary fraction of a solid body electrolyte.

According to the present invention, the solid body electrolyte can comprise more than two electrodes, which in sum are made of pure platinum, a gold alloy and/or a doped platinum, on its top side. According to the present invention, the solid body electrolyte can just as well comprise more than one electrode, which in sum is made of pure platinum and/or a doped platinum, on its bottom side. According to the present invention, these can also comprise different compositions.

The measurement of the gas concentrations of the oxidizable gases by a gas sensor is done using a non-equilibrium voltage (a so-called non-Nernst voltage) on the mixed potential electrode and an equilibrium voltage on the two electrodes made of the pure platinum or doped platinum (a so-called Nernst voltage resulting from the potential between the two electrodes made of the pure platinum or doped platinum), whereby these voltages allow the amount of oxidizable gases in the gas mixture flowing past the gas sensor, and thus the gas concentration thereof, to be determined. Preferably, an oxidizing gas is determined in the presence of three electrodes.

In this context, the equilibrium voltage on the two electrodes made of the pure platinum or doped platinum is determined by an (electrical) resistor that is connected to the Pt electrode situated on the top side of the solid body electrolyte. The (electrical) resistor is preferably arranged in a gas sensor device, which comprises the gas sensor as well.

By continuously pumping oxygen ions in and out in accordance with the explanations provided in DE 196 51 328 B4, the resulting equilibrium voltage allows the oxygen gas concentration in the gas mixture to be determined continuously in the exhaust gas flow according to the preceding explanations.

Moreover, the gas concentration, for example of carbon monoxide, can be determined by the gas sensor described above.

The values determined in the respective measurement of the equilibrium voltage in the platinum electrode (i.e., the electrode made of pure platinum or doped platinum) and the non-equilibrium voltage on the electrode made of the gold alloy are converted, for example, by a data processing facility, such that percentage weight fractions of the gases can be determined and presented.

With regard to the layout of a gas sensor and moreover the measuring methods of a gas sensor, reference shall be made to documents DE 10 2007 048 049 A1, DE 197 57 112 A1, and DE 196 51 328 B4.

The gas sensor 1 shown in FIG. 1 for measuring the concentrations of gases, in particular of oxygen and at least one further gas (i.e., carbon monoxide in the exemplary embodiment), is part of a gas sensor device 2 that is shown in FIG. 1. Referring to FIG. 1, the gas sensor device 2 comprises electrical connectors, a control or regulation unit or the like such that the data delivered by the gas sensor 1 during a measurement can be analyzed.

It is feasible to use the gas sensor 1 for measuring gas concentrations, for example, in an exhaust gas pipe of a gas or oil heating system, such that the oxygen concentration ($O_2$ concentration) and the carbon monoxide concentration (CO concentration) can be determined, for example in the exhaust gas flow, by the gas sensor 1 and thus also by the gas sensor device 2.

The gas sensor 1 is arranged on a ceramic substrate (i.e., on a substrate 3 made of $ZrO_2$ in the exemplary embodiment) that is insulating.

The gas sensor 1 further comprises a solid body electrolyte, which is a solid body electrolyte 4 made of at least 90% by weight $ZrO_2$ doped with 1 to 10% by weight yttrium oxide or 1 to 10% by weight hafnium oxide in the exemplary embodiment.

Moreover, the gas sensor 1 comprises three electrodes 5a, 5b, 6. In the exemplary embodiment, two electrodes are each an electrode 5a, 5b made of doped platinum and the third electrode is an electrode 6 made of a gold alloy.

The one electrode 5a made of the doped platinum is arranged on the top side 4a of the solid body electrolyte 4 and the electrode 6 made of the gold alloy is also arranged on the top side 4a of the solid body electrolyte 4. The further electrode 5b made of the doped platinum is arranged on the bottom side 4b of the solid body electrolyte 4 according to FIG. 1.

The electrodes 5a, 5b on the solid body electrolyte 4 in the exemplary embodiment each consist of the same doped platinum, which comprises a composition of 0.5% by weight to 15% by weight $ZrO_2$ and the remainder being pure platinum in the exemplary embodiment. The electrodes 5a, 5b made of the doped platinum preferably are provided to be porous such that they allow oxygen ions to pass.

The electrode 6 provided as a gold alloy according to the explanations above comprises an alloy composition of approximately 85% by weight gold and approximately 15% by weight platinum in the exemplary embodiment. Accordingly, the ratio is 85% gold to 15% platinum, whereby no solid body electrolyte is admixed in the exemplary embodiment.

Alternatively, it is feasible to add a $ZrO_2$ fraction to electrode 6, which comprises a gold alloy at a ratio of 85% gold and 15% platinum. A $ZrO_2$-doped gold alloy of this type is also known as doped gold alloy.

It is feasible just as well that the gold alloy and the doped platinum comprise impurities, though these are negligible from a technical point of view and were generated during the production. The fractions thereof are to be neglected for the gas concentration measurements.

Consisting of the gold alloy, electrode 6 comprises a layer thickness of approximately 5 μm in the exemplary embodiment.

The distance A between the electrodes 5a, 6 on the top side 4a of the solid body electrolyte 4 preferably is approximately 300 μm in the exemplary embodiment.

In the exemplary embodiment, the electrodes 5a, 5b, 6 have been applied firmly on the wall (i.e., on the corresponding top side 4a and bottom side 4b) of the solid body electrolyte 4 by screen printing.

The gas sensor 1 further comprises a closed chamber 7, whereby, according to FIG. 1, the bottom side 4b of the solid body electrolyte 4 and the electrode 5b made of the doped platinum together form a part of the chamber 7. According to FIG. 1, the electrode 5b made of the doped platinum and the solid body electrolyte 4 therefore form a wall of the chamber 7.

The other wall of the chamber 7 is formed by the substrate 3 made of $ZrO_2$. The other wall comprises a spacing in the form of a distance with respect to the underside 4b of the solid body electrolyte 4 together with the electrode 5b.

Moreover, the spacing in the form of the distance according to FIG. 1 leads to the formation of side walls for the chamber 7, such that a closed chamber is formed when the side walls are closed. The side walls are closed by an insulating glass seal 8 in the exemplary embodiment. In this context, the side walls form an edge and/or the edges of the chamber 7 in the side region. Moreover, a platinum paste 9 is situated in the region of each of the side walls of the gas sensor 1, whereby the respective platinum paste 9, according to FIG. 1, is situated right inside the chamber 7.

The electrode 5a is intended for pumping oxygen into and out of the chamber 7.

FIG. 1 shows no resistor by which the oxygen gas concentration of an in-flowing gas flow can be measured by the gas sensor 1.

FIG. 1 also does not show a heating conductor of the type of a heat conductor for being able, for example, to use the gas sensor 1 with exhaust gases that are not yet at an optimal temperature, in order to enable an optimal ion transport, which proceeds more easily and better at higher temperature, in the solid body electrolyte 4 made of $ZrO_2$.

By the gas sensor 1 according to FIG. 1, an oxidizable exhaust gas component, for example carbon monoxide, can be measured in addition to the oxygen concentration, for example in an exhaust gas pipe. In the exemplary embodiment, a single exhaust gas component in the form of an oxidizable gas, namely carbon monoxide, is measured.

Alternatively or in addition, it is feasible to measure other gas concentrations, such as the hydrogen concentration, the nitrogen concentration or the like by the gas sensor 1 and by the gas sensor device 2.

For measuring, a gas mixture flows about the top side 4a of the solid body electrolyte 4. The measurement of the gas concentrations of the oxidizable gases by the gas sensor 1 is done by a non-equilibrium voltage on the mixed potential electrode, being the electrode 6 made of the gold alloy in the present case, and an equilibrium voltage on the two electrodes 5a, 5b made of the doped platinum, whereby these voltages allow not only the oxygen amount, but also the amount of oxidizable gases, being just carbon monoxide in the present case, in the gas mixture flowing past the gas sensor 1, and thus the gas concentration thereof, to be determined.

In this context, the equilibrium voltage on the two electrodes 5a, 5b made of the doped platinum is determined by an (electrical) resistor that is connected to the Pt electrode 5a situated on the top side of the solid body electrolyte. The (electrical) resistor is preferably arranged in the gas sensor device 2, which comprises the gas sensor 1 as well. The resistor is not shown in FIG. 1.

The determination and conversion are known from DE 197 57 112 A1 and DE 10 2007 048 049 A1.

The gas sensor 1 shown in FIG. 1 can be produced by a device for producing gas sensors 1.

The gas sensor 1 shown in FIG. 1 can be produced by a method for producing gas sensors 1, in which the gas sensor 1 is produced by the device for producing gas sensors 1.

In the exemplary embodiment, the gas sensor 1 is used for measuring by a method for measuring concentrations of gases, in particular oxygen and at least one further gas, preferably at least one oxidizable exhaust gas component.

It is feasible, for example, to arrange the gas sensor 1 in the exhaust gas pipe of a heating system, whereby the exhaust gas of the gas or oil mixture combusted in the heating system comprises a gas mixture that can be measured by the gas sensor 1. Accordingly, it is feasible, for example, to continuously measure, in the exhaust gas pipe, the oxygen concentration and the carbon monoxide concentration of the exhaust gas by the gas sensor 1.

Moreover, in addition, it is feasible to adjust the exhaust gas concentration by the heating system by continuously adjusting the gas concentration in the exhaust gas to optimal values, such that optimal utilization of the efficiency of the gas or oil mixture supplied to the heating system is rendered possible if the gas composition of the exhaust gas is made known continuously by the gas sensor 1.

Alternatively, it is feasible just as well to use the gas sensor 1 described above in a power plant, in a baking oven, in a car or in a container.

The use of the gas sensor 1, for example in a container, provides for optimal monitoring and adjustment of the storage of fruit or the like in a container of this type for transports, for example, by air or ship routes.

Figure 2:
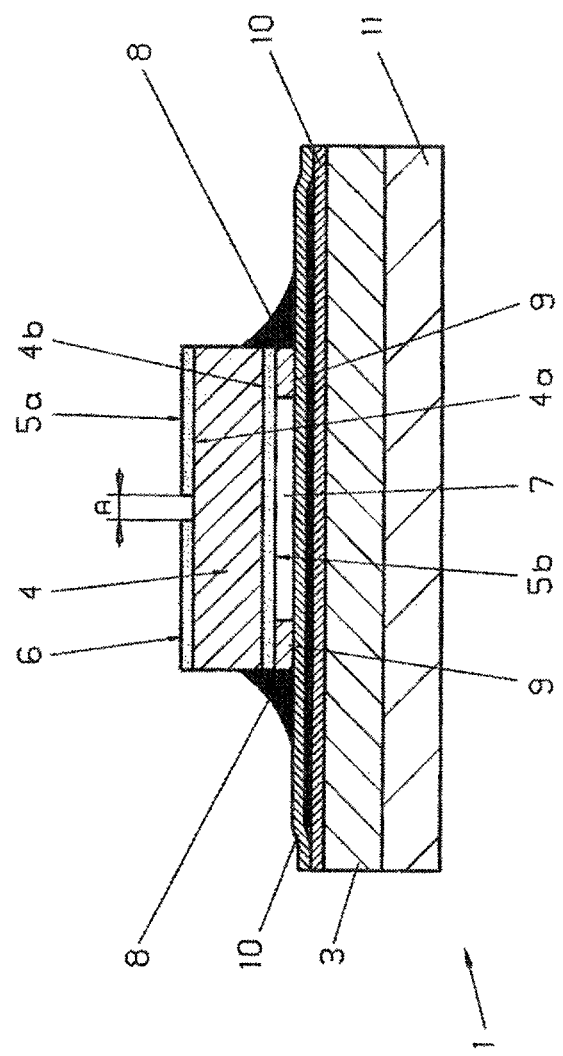
FIG. 2 shows a detail of another design of a gas sensor 1 according to an embodiment of the present invention.

Only the features deviating from FIG. 1 shall be described for the gas sensor 1 presented in FIG. 2.

Identical components of the gas sensor 1 are provided with the same reference numbers in FIG. 2 and different components are provided with new reference numbers in FIG. 2.

The gas sensor 1 shown in FIG. 2, which is part of a gas sensor device 2, comprises a platinum heater 11 in the form of a heating conductor. In this context, the platinum heater 11 is arranged on the substrate 3 according to FIG. 2 below the substrate 3 of the gas sensor 1. In this context, the platinum heater 11 is joined to the substrate 3. Moreover, the gas sensor 1 comprises a two-layered glass passivation 10 on the top side of the substrate 3 of the gas sensor 1 according to FIG. 2, whereby the glass passivation 10 forms a part of the wall of the chamber 7 according to FIG. 2.

By the platinum heater 11, it is feasible to adjust the operating temperature of the gas sensor 1 appropriately such that a precise, rapid, and simple measurement of the exhaust gas composition is made feasible, in particular at low temperatures. This is the case, because the heating conductor heats the gas sensor 1 when the temperature is too low for the measurement to be optimal and rapid.

Figure 3:
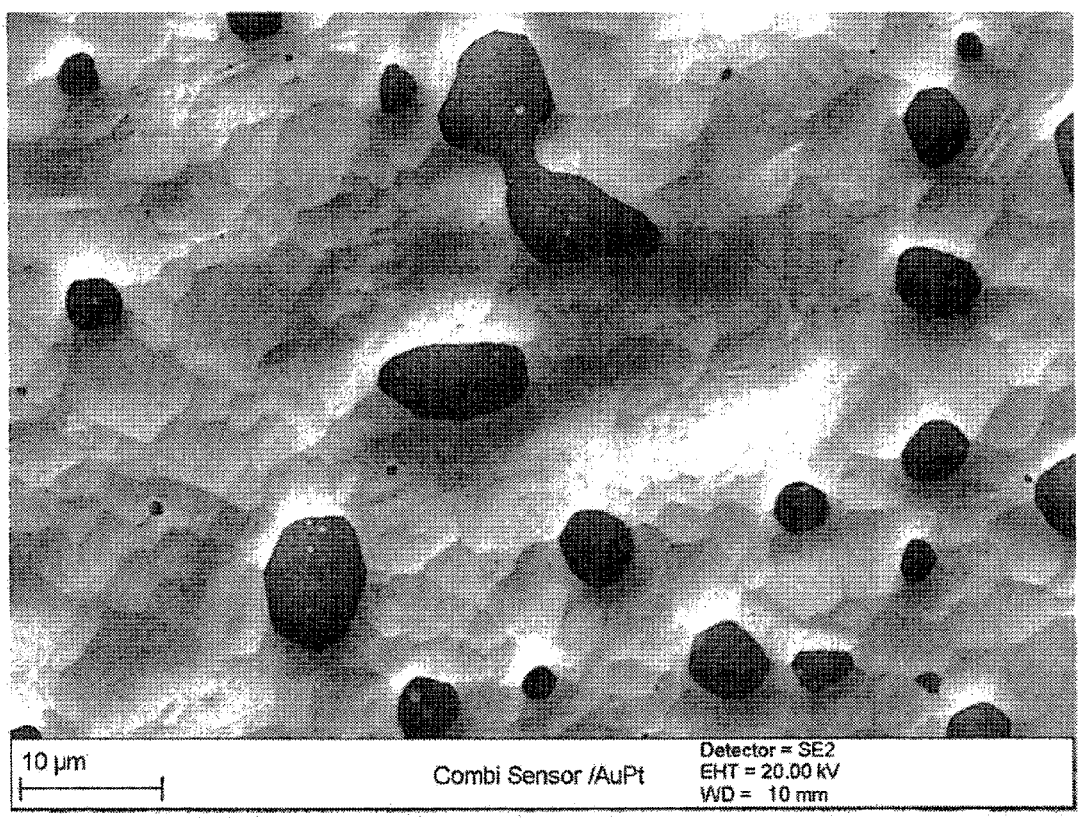
FIG. 3 shows a scanning electron micrograph of an Au electrode according to an embodiment of the present invention.

FIG. 3 shows a scanning electron micrograph at 1,500-fold magnification. The image shows an electrode 6 that comprises a composition according to the present invention. Accordingly, the gold alloy comprises at least gold and platinum at a ratio of 85% gold to 15% platinum. According to FIG. 3, the porosity of the electrode 6 is very low.

Figure 4:
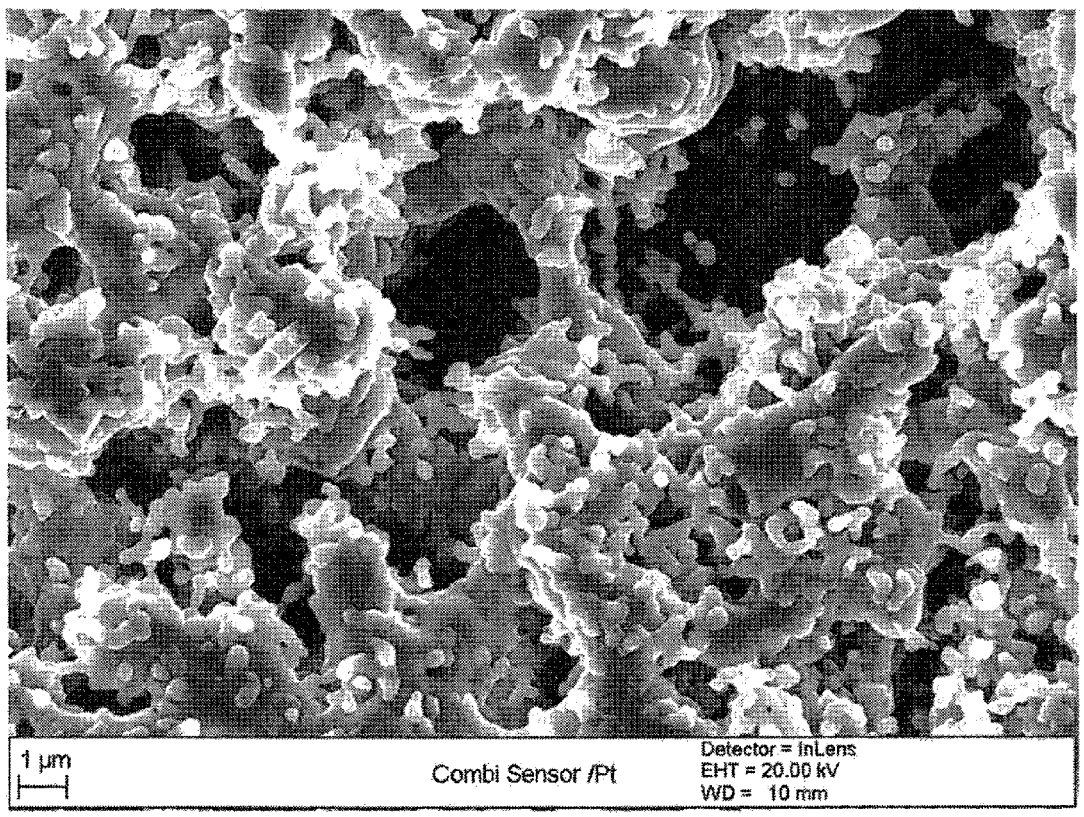
FIG. 4 shows a scanning electron micrograph of a Pt electrode according to an embodiment of the present invention.

FIG. 4 shows another scanning electron micrograph at 3,000-fold magnification. In this context, FIG. 4 shows an image of an electrode 5a that comprises a composition according to the present invention. According to FIG. 4, the porosity of the electrode 5a is very high.

FIGS. 3 and 4 are shown true to scale.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A gas sensor for measuring the concentrations of gases, in particular of oxygen and at least one oxidizable exhaust gas component in the form of a further gas, the gas sensor comprising:

at least one solid body electrolyte made of at least $ZrO_2$, a remainder of the at least one solid body electrolyte being made of at least one further element selected from the group consisting of yttrium oxide and hafnium oxide;

at least three electrodes comprising two electrodes made of at least doped platinum and one electrode made of a gold alloy, wherein one of the electrodes made of at least doped platinum and the one electrode made of the gold alloy are arranged on a top side of the solid body electrolyte, and the other of the electrodes made of at least doped platinum is arranged on a bottom side of the solid body electrolyte that is situated opposite from the top side;

at least one closed chamber, wherein the bottom side of the solid body electrolyte forms a part of the closed chamber, wherein the doped platinum of the two electrodes comprises at least 50% by weight platinum and a remainder comprises at least one further element selected from the group of the solid body electrolytes; and only one heating conductor.

2. The gas sensor according to claim 1, wherein the doped platinum of the two electrodes consists of between 0.5% by weight to 15% by weight $ZrO_2$ and the remainder is platinum.

3. The gas sensor according to claim 1, wherein the gold alloy comprises at least 50% by weight gold and maximally 50% by weight platinum.

4. The gas sensor according to claim 1, wherein the gold alloy comprises approximately 85% by weight gold and approximately 15% by weight platinum.

5. The gas sensor according to claim 1, wherein the gold alloy comprises at least gold and platinum at a ratio of 85% gold to 15% platinum.

6. The gas sensor according to claim 5, wherein the gold alloy further comprises at least 0.5% by weight to 15% by weight of a solid body electrolyte.

7. The gas sensor according to claim 1, wherein the at least one solid body electrolyte is made of at least 90% by weight $ZrO_2$.

8. The gas sensor according to claim 1, wherein the one electrode made of the gold alloy comprises a layer thickness from 0.1 μm to 50 μm.

9. The gas sensor according to claim 1, wherein a distance (A) between the electrodes on the top side of the solid body electrolyte is between 100 μm and 500 μm.

10. The gas sensor according to claim 1, wherein the three electrodes are configured to be applied to the solid body electrolyte (4) by screen printing or by dispensing.

11. The gas sensor according to claim 1, wherein the at least one oxidizable exhaust gas components is selected from the group consisting of hydrogen compounds, nitrogen compounds, ammonia compounds, carbon compounds, and hydrocarbons.

12. The gas sensor according to claim 1, wherein the at least one gas sensor is arranged on a ceramic substrate.

13. A method for measuring concentrations of gases, in particular of oxygen and at least one oxidizable exhaust gas component in the form of a further gas, the method comprising measuring concentrations of the gases using the gas sensor according to claim 1.

* * * * *